(12) United States Patent
Phares

(10) Patent No.: US 8,349,892 B2
(45) Date of Patent: Jan. 8, 2013

(54) SOLID FORMULATIONS OF PROSTACYCLIN ANALOGS

(75) Inventor: Kenneth R. Phares, Hillsborough, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 261 days.

(21) Appl. No.: 12/775,102

(22) Filed: May 6, 2010

(65) Prior Publication Data

US 2010/0282622 A1 Nov. 11, 2010

Related U.S. Application Data

(60) Provisional application No. 61/176,268, filed on May 7, 2009.

(51) Int. Cl.
*A01N 37/08* (2006.01)
*A61K 31/215* (2006.01)

(52) U.S. Cl. .................. 514/530; 514/532; 424/451

(58) Field of Classification Search ............ 514/530, 514/532

See application file for complete search history.

(56) References Cited

U.S. PATENT DOCUMENTS

| | | |
|---|---|---|
| 4,306,075 A | 12/1981 | Aristoff |
| 5,153,222 A | 10/1992 | Tadepalli et al. |
| 5,234,953 A | 8/1993 | Crow et al. |
| 6,054,486 A | 4/2000 | Crow et al. |
| 6,521,212 B1 | 2/2003 | Cloutier et al. |
| 6,756,033 B2 | 6/2004 | Cloutier et al. |
| 6,765,117 B2 | 7/2004 | Moriarty et al. |
| 6,803,386 B2 | 10/2004 | Shorr et al. |
| 6,809,223 B2 | 10/2004 | Moriarty et al. |
| 7,199,157 B2 | 4/2007 | Wade et al. |
| 7,384,978 B2 | 6/2008 | Phares et al. |
| 7,417,070 B2 | 8/2008 | Phares et al. |
| 7,544,713 B2 | 6/2009 | Phares et al. |
| 2004/0265238 A1 | 12/2004 | Chaudry |
| 2005/0085540 A1* | 4/2005 | Phares et al. .................. 514/530 |
| 2005/0101608 A1 | 5/2005 | Santel |
| 2005/0165111 A1 | 7/2005 | Wade et al. |
| 2005/0282901 A1 | 12/2005 | Phares et al. |
| 2005/0282903 A1 | 12/2005 | Wade et al. |
| 2006/0194842 A1 | 8/2006 | Uchida et al. |
| 2006/0222792 A1 | 10/2006 | Braverman et al. |
| 2007/0078095 A1 | 4/2007 | Phares et al. |
| 2007/0082948 A1 | 4/2007 | Phares et al. |
| 2007/0254032 A1 | 11/2007 | Kidane et al. |
| 2008/0200449 A1 | 8/2008 | Olschewski et al. |
| 2008/0249167 A1 | 10/2008 | Phares et al. |
| 2008/0280986 A1 | 11/2008 | Wade et al. |
| 2008/0299185 A1* | 12/2008 | Ortenzi et al. ............... 424/451 |
| 2009/0163738 A1 | 6/2009 | Batra et al. |
| 2009/0281129 A1 | 11/2009 | Chang et al. |

FOREIGN PATENT DOCUMENTS

WO WO 2005/007081 A2 1/2005

OTHER PUBLICATIONS

International Search Report and Written Opinion mailed Aug. 4, 2010, in corresponding PCT/US2010/033852, 8 pages.

* cited by examiner

*Primary Examiner* — Mina Haghighatian
(74) *Attorney, Agent, or Firm* — Foley & Lardner LLP

(57) ABSTRACT

Moderate moisture levels, such as greater than 3% but no greater than 7%, may be beneficial for solid formulations of certain prostacyclin analogs. Accordingly, a solid formulation containing a prostacyclin analog may be packaged inside a pharmaceutical packaging with such amount of a desiccant or a drying agent that after the storage the solid formulation may have a moderate level of moisture in it.

33 Claims, No Drawings

SOLID FORMULATIONS OF PROSTACYCLIN ANALOGS

RELATED APPLICATIONS

The present application claims priority and incorporates by reference in its entirety U.S. provisional application No. 61/176,268 filed May 7, 2009.

FIELD

The present inventions relate to pharmaceutical formulations of prostacyclin analogs and their storage methods and, in particular, to solid formulations of prostacyclin analogs and their storage methods.

SUMMARY

According to one embodiment, a pharmaceutical product comprises a pharmaceutical packaging configured to maintain a moisture level of greater than 3% and no more than 7%; and a solid formulation inside the packaging, wherein the formulation comprises a active agent having formula I:

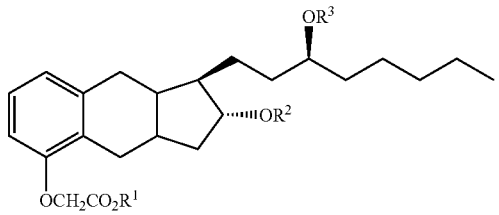

wherein $R^1$ is independently selected from the group consisting of H, substituted and unsubstituted benzyl groups, and groups wherein $OR^1$ are substituted or unsubstituted glycolamide esters; $R^2$ and $R^3$ may be the same or different and are independently selected from the group consisting of H, phosphate and groups wherein $OR^2$ and $OR^3$ form esters of amino acids or proteins, or an enantiomer or a pharmaceutically acceptable salt thereof.

According to another embodiment, a pharmaceutical product comprises (a) a pharmaceutical packaging; (b) a solid formulation inside the packaging, wherein the formulation comprises a active agent having formula I:

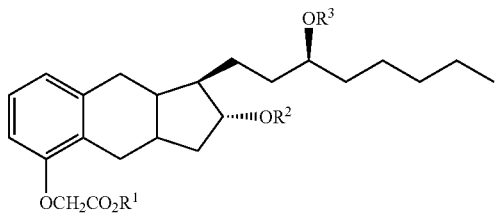

wherein $R^1$ is independently selected from the group consisting of H, substituted and unsubstituted benzyl groups, and groups wherein $OR^1$ are substituted or unsubstituted glycolamide esters; $R^2$ and $R^3$ may be the same or different and are independently selected from the group consisting of H, phosphate and groups wherein $OR^2$ and $OR^3$ form esters of amino acids or proteins, or an enantiomer or a pharmaceutically acceptable salt thereof; (c) a desiccant inside the packaging, wherein an amount of the desiccant in the packaging is less than an effective amount for maintaining a relative humidity level inside the packaging for a storage time of the formulation below 40%. Yet according to another embodiment, a storage method comprising: storing a solid formulation inside a pharmaceutical packaging, wherein the formulation comprises an active agent having formula I:

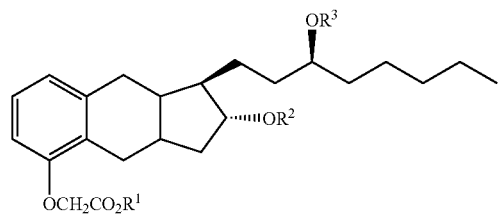

wherein $R^1$ is independently selected from the group consisting of H, substituted and unsubstituted benzyl groups, and groups wherein $OR^1$ are substituted or unsubstituted glycolamide esters; $R^2$ and $R^3$ may be the same or different and are independently selected from the group consisting of H, phosphate and groups wherein $OR^2$ and $OR^3$ form esters of amino acids or proteins, or an enantiomer or a pharmaceutically acceptable salt thereof; wherein a moisture level in the solid formulation after said storing is greater than 3% and no more than 7%.

And yet in another embodiments, a storage method comprises storing a solid formulation and a desiccant inside a pharmaceutical packaging, wherein the formulation comprises an active agent having formula I:

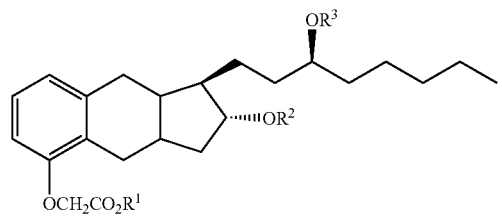

wherein $R^1$ is independently selected from the group consisting of H, substituted and unsubstituted benzyl groups, and groups wherein $OR^1$ are substituted or unsubstituted glycolamide esters; $R^2$ and $R^3$ may be the same or different and are independently selected from the group consisting of H, phosphate and groups wherein $OR^2$ and $OR^3$ form esters of amino acids or proteins, or an enantiomer or a pharmaceutically acceptable salt thereof; wherein an amount of the desiccant is less that an effective amount for maintaining a relative humidity level inside the packaging during said storing below 40%.

DETAILED DESCRIPTION

Unless otherwise specified "a" or "an" means to one or more.

Typically, pharmaceutical compounds in solid formulations are considered to be more stable when they are stored at a humidity level, which is as low as possible, so that a moisture level in the stored solid formulation is as low as possible as well. Therefore, solid formulations containing one or more pharmaceutical compounds are typically packaged with an effective amount of a drying agent or desiccant so that the drying agent or desiccant maintains the humidity level inside the packaging at a low level, which may be, for example, below 40% relative humidity for a storage temperature during the whole storage time.

The present inventor discovered that a moderate moisture level may be beneficial for solid formulations of certain prostacyclin analogs. In particular, the moderate moisture level in such formulations may result in less degradation and/or less unfavorable impurities compared to a formulation with a minimal moisture content, which may be a moisture level below 3%.

Accordingly, in some embodiments, a pharmaceutical product may comprise a pharmaceutical packaging configured to maintain a moderate moisture level inside the packaging and a solid formulation comprising, as an active agent, a prostacyclin analog. Particular prostacyclin analogs, which may be used as an active agent are disclosed in the section "Active agent".

In certain cases, the moderate moisture level may be a level that is greater than 3% and less than a moisture level effective to dissolve a component of the formulation. For example, the moderate moisture level may be greater than 3% and no greater than 7%; or greater than 3% and no greater than 6%; or greater than 3% and no greater than 5.5%; or greater than 3% and no greater than 5%; or greater than 3% and no greater than 4.5%; no less than 3.5% and no greater than 7%; or no less than 3.5% and no greater than 6%; or no less than 3.5% and no greater than 5%; or no less than 3.5% and no greater than 4.5%. Procedures for measuring moisture levels in solid form formulations are known to those of ordinary skill in the art.

The present invention allows using for storing inside a pharmaceutical packaging a solid pharmaceutical formulation, which may contain a prostacyclin analog as defined below, a reduced amount of a desiccant or a drying agent, which is less than an amount of the desiccant or the drying agent necessary to maintain a relative humidity below 40% during the whole storing time of a pharmaceutical product. Reducing the amount of a desiccant or a drying agent may lower a cost of the pharmaceutical product. For example, if X grams of desiccant or a drying agent is required to maintain a relative humidity for a storage temperature at a level below 40% inside the pharmaceutical packaging during a storage time, the reduced amount of the desiccant drying agent may be no more than 0.9 X grams or no more than 0.85 X grams or no more than 0.8 X grams or no more than 0.75 X grams or no more than 0.7 X grams or no more than 0.65 X grams or no more than 0.6 X grams or no more than 0.55 X grams or no more than 0.5 X grams or no more than 0.45 X grams or no more than 0.4 X grams or no more than 0.35 X grams or no more than 0.3 X or no more than 0.25 X or no more than 0.2 X. Preferably, the reduced amount of the desiccant or the drying agent that the solid formulation at the end of the storage time has a moderate moisture level as defined above. The actual reduced amount of a desiccant or drying agent may depend on a number of factors, such as a volume of the unit packaging; a type of the packaging, a seal applied to the packaging, such as a cap; a type of desiccant; a storage time; storage conditions, such as temperature and a relative outside humidity; an amount of the pharmaceutical formulation in the unit packaging.

The storage time for the product may be 1 month, 2 months, 3 months, 6 months, 9 months, 12 months, 18 months, 24 months, 30 months or 36 months or 42 months or 48 months. The storage conditions may include a storage temperature ranging from 10° C. to 55° C., 15° C. to 50° C. or from 15° C. to 45° C. or any temperature within these ranges and a relative outside humidity (humidity outside the packaging) ranging from 20% to 100% or from 30% to 90% or from 40% to 85% or any integer within these ranges. Exemplary storage conditions may be 25 C/60% relative humidity (RH), 30 C/75% RH, and 40 C/75% RH.

The packaging may be any pharmaceutical packaging known in the pharmaceutical arts. In some embodiments, the packaging may be a bottle packaging, such as a glass or a plastic bottle. Plastic bottles for pharmaceutical packaging may be bottles made of a polymer material, such as high density polyethylene (HDPE).

Yet in some other embodiments, the packaging may be a blister pack. The blister pack may include a forming component and a covering or lidding component, which may be sealed or attached to the forming component. The forming component of the blister pack may be shaped to hold a solid dose formulation, such as tablet or capsule formulation. The forming component may be composed of a metal, such as aluminum, or a blister-packaging plastic or polymer material, such as polyvinyl chloride (PVC), polyvinylidene chloride (PVDC), Polychlorotrifluoroethylene (PCTFE, commercially sold as ACLAR®), or polypropylene (PP). The covering or lidding component may include a support material, such as aluminum, which can have a sealing agent, such as a heat sealing agent, disposed on one side.

In some embodiments, the packaging may be such that it may maintain the moderate moisture level (as defined above) in the formulation during the storage time of the pharmaceutical product, which may be 1 month, 2 months, 3 months, 6 months, 9 months, 12 months, 18 months, 24 months, 30 months or 36 months or 42 months or 48 months under storage conditions, which may include a storage temperature ranging from 10° C. to 55° C., 15° C. to 50° C. or from 15° C. to 45° C. or any temperature within these ranges and a relative outside humidity (humidity outside the packaging) ranging from 20% to 100% or from 30% to 90% or from 40% to 85% or any integer within these ranges.

In some embodiments, a combination of a) the amount of a desiccant or a drying agent and b) the packaging may be such that it may maintain a humidity level inside the packaging such that a pharmaceutical composition has a moderate moisture level (as defined above) during the storage time of the product, which may be 1 month, 2 months, 3 months, 6 months, 9 months, 12 months, 18 months, 24 months, 30 months or 36 months or 42 months or 48 months under storage conditions, which may include a storage temperature ranging from 10° C. to 55° C., 15° C. to 50° C. or from 15° C. to 45° C. or any temperature within these ranges and a relative outside humidity ranging from 20% to 100% or from 30% to 90% or from 40% to 85% or any integer within these ranges.

A desiccant or a drying agent may be any desiccant or drying agent, which is used in pharmaceutical arts. For example, the desiccant may be bentonite, such sodium bentonite or calcium bentonite; molecular sieve, activated carbon, silica gel or any combination thereof.

In some embodiments, the pharmaceutical product may be such that it is does not contain a desiccant or a drying agent. Omitting a desiccant/drying agent may lower a cost of the pharmaceutical product.

The solid formulation may be a solid dose formulation, such as a tablet or a capsule, which may be directly administered to a patient. The solid formulation may be also in an intermediate form, such as a powder, from which a solid dose formulation, such as a tablet or a capsule, may be formed.

In some embodiments, a mass of the individual solid dose formulation, such as may be from 10 mg to 1 g or from 20 mg or 500 mg or from 50 mg to 400 mg or any subrange within these ranges. For example, a core of the tablet or capsule, without a coating, such as a functional or color coating, may have a mass of about 200 mg.

A mass of the active agent, such as a prostacyclin analog, in the individual solid dose formulation may vary. For example, when the active agent is treprostinil diethanolamine, its mass per the individual solid dose formulation, such as a tablet or capsule, may vary from 0.01 mg to 50 mg or 0.02 mg to 20 mg or from 0.05 mg to 10 mg or any subrange within these ranges. Exemplary mass of treprostinil per individual solid dose formulation may be 0.125 mg, 0.25 mg, 0.5 mg, 1 mg and 2.5 mg or if recalculated in a mass of treprostinil diethanolamine, 0.125×1.27 mg, 0.25×1.27 mg, 0.5×1.27 mg, 1×1.27 mg and 2.5×1.27 mg, respectively.

In addition to the active agent, the solid formulation may also include one or more pharmaceutically acceptable excipients. When the active agent in the solid formulation is treprostinil diethanolamine, the core excipients may include maltodextrin, sodium lauryl sulfate, magnesium stearate and/or xylitol.

An exemplary pharmaceutical product may include 100 tablets containing treprostinil diethanolamine placed inside of a plastic pharmaceutical bottle, which may be a 45 cc HDPE bottle together with less 1 g of desiccant, such as bentonite clay or silica gel. The amount of desiccant in such product may be 0.5 mg or less. The product may also contain a stopper or holder, which may prevent the tablets from moving within the bottle and/or breaking apart. Such a stopper or holder may be, for example, a coil, such as a rayon coil.

A solid dose formulation may be prepared by compressing a powder comprising an active agent disclosed below in the section "Active agent".

In addition to the active agent, the powder may contain one or more excipients, such as those disclosed above for treprostinil diethanolamine.

A mass of the powder for forming a solid dose formulation may vary. For example, a solid dose formulation may require from 10 mg to 1000 mg of the powder or from 20 mg to 500 mg or from 50 mg to 400 mg or from 100 mg to 300 mg or from 150 mg to 250 mg or any integer within these ranges.

A mass concentration of the active agent in the powder may also vary. For example, the mass concentration of the active agent in the powder may be from 0.02% to 3%, or from 0.03% to 2.5% or from 0.05% to 2%.

An exemplary mass of the powder for forming a solid dose formulation may be 200 mg. For preparation of such solid dose formulation, for a dose of 0.125 mg of treprostinil (0.125×1.27 mg of treprostinil diethanolamine) in the formulation, a mass concentration of the active agent in the powder can be about 0.079%; for a dose of 0.25 mg (0.25×1.27 mg of treprostinil diethanolamine), about 0.159%; for a dose of about 0.5 mg (0.5×1.27 mg of treprostinil diethanolamine), 0.317%; for a dose of 1 mg (1×1.27 mg of treprostinil diethanolamine), about 0.63%; for a dose of 2.5 mg (2.5×1.27 mg of treprostinil diethanolamine), about 1.59%.

The solid dose formulations may prepared from the powder using a press. Presses for preparation solid state formulations are common in the pharmaceutical industry.

A moisture level in the powder before pressing may be no more or less than 3%. After pressing the solid dose formulation may placed inside a pharmaceutical packaging, such a as a bottle, for storing. In addition to the solid dose formulation, one may also place inside the pharmaceutical packaging a desiccant or a drying agent. In some embodiments, the placed amount of the desiccant or the drying agent may be less than an effective amount that is necessary for maintaining a humidity level below 40% inside the pharmaceutical packaging for a storage time of the formulation, which may be 1 month, 2 months, 3 months, 6 months, 9 months, 12 months, 18 months, 24 months, 30 months or 36 months or 42 months or 48 months. For example, the placed amount of the desiccant or the drying agent may be at most 90% or at most 85% or at most 80% or at most 75% or at most 70% or at most 65% or at most 60% or at most 55% or at most 50% or at most 45% or at most 40% or at most 35% or at most 30% or at most 25% or at most 20% of the effective amount that is necessary for maintaining a relative humidity level below 40% inside the pharmaceutical packaging for the storage time of the formulation. In some embodiments, the placed amount of the desiccant or the drying agent may be such that at the end of the storage time the formulation has a moderate moisture level as defined above.

After the storage time, the solid dose formulation may be removed from the packaging and administered to a subject, such as a human being.

Active Agent

In some embodiments, the active agent may be a compound of formula I:

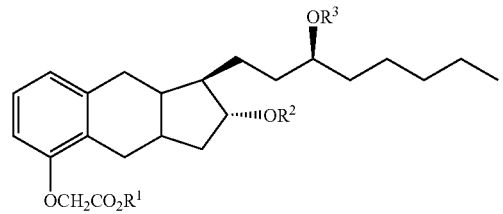

wherein, $R^1$ is independently selected from the group consisting of H, substituted and unsubstituted benzyl groups and groups wherein $OR^1$ are substituted or unsubstituted glycolamide esters; $R^2$ and $R^3$ may be the same or different and are independently selected from the group consisting of H, phosphate and groups wherein $OR^2$ and $OR^3$ form esters of amino acids or proteins, enantiomers of the compound; and pharmaceutically acceptable salts of the compound.

In some embodiments, wherein $OR^1$ are substituted or unsubstituted glycolamide esters, $R^1$ is —$CH_2CONR^4R^5$ and $R^4$ and $R^5$ may be the same or different and are independently selected from the group consisting of H, OH, substituted and unsubstituted alkyl groups, —$(CH_2)_mCH_3$, —$CH_2OH$, and —$CH_2(CH_2)_{10}H$, with the proviso that m is 0, 1, 2, 3 or 4, and n is 0, 1, 2, 3 or 4.

One skilled in the art will also readily recognize that where members are grouped together in a common manner, such as in a Markush group or the groups described in the R of structures I and II above and below, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention. For example, $R^1$ can specifically exclude H, substituted and unsubstituted benzyl groups, or groups wherein $OR^1$ are substituted or unsubstituted glycolamide esters. In some embodiments, $R^1$ is a substituted or unsubstituted benzyl groups, such as —$CH_2C_6H_5$, —$CH_2C_6H_4NO_2$, —$CH_2C_6H_4OCH_3$, —$CH_2C_6H_4Cl$, —$CH_2C_6H_4(NO_2)_2$, or —CH$_2$C$_6$H$_4$F. The benzyl group can be ortho, meta, para, ortho/para substituted and combinations thereof. Suitable substituents on the aromatic ring include halogens (fluorine, chlorine, bromine, iodine), —NO$_2$ groups, —OR$^{16}$ groups wherein R$^{16}$ is H or a C$_1$-C$_4$ alkyl group, and combinations thereof.

Alternatively, when R$^1$ is —CH$_2$CONR$^4$R$^5$ then R$^4$ and R$^5$ may be the same or different and are independently selected from the group consisting of H, OH, —CH$_3$, and —CH$_2$CH$_2$OH. In these compounds where R$^1$ is not H, generally one or both of R$^2$ and R$^3$ are H.

In some embodiment one or both of R$^2$ and R$^3$ are H and R$^1$ is —CH$_2$CONR$^4$R$^5$, and one or both of R$^4$ and R$^5$ are H, —OH, —CH$_3$, —CH$_2$CH$_2$OH.

In compounds where one or both of R$^2$ and R$^3$ are not H, R$^2$ and R$^3$ can be independently selected from phosphate and groups wherein OR$^2$ and OR$^3$ are esters of amino acids, dipeptides, esters of tripeptides and esters of tetrapeptides. In some embodiments, only one of R$^2$ or R$^3$ is a phosphate group. In compounds where at least one of R$^2$ and R$^3$ is not H, generally R$^1$ is H. In additional embodiments, one of R$^2$ and R$^3$ are H and thus the compound of structure I is derivatized at only one of R$^2$ and R$^3$. In particular compounds, R$^2$ is H and R$^3$ is defined as above. In additional embodiments, R$^1$ and R$^3$ are H and R$^2$ is a group wherein OR$^2$ is an ester of an amino acid or a dipeptide. In further embodiments, R$^1$ and R$^2$ are H and R$^3$ is a group wherein OR$^3$ is an ester of an amino acid or a dipeptide.

When one or both of the OR$^2$ and OR$^3$ groups form esters of amino acids or peptides, i.e., dipeptides, tripeptides or tetrapeptides, these can be depicted generically as —COCHR$^6$NR$^7$R$^8$ wherein R$^6$ is selected from the group consisting of amino acid side chains, R$^7$ and R$^8$ may be the same or different and are independently selected from the group consisting of H, and —COCHR$^9$NR$^{10}$R$^{11}$. Generally, reference to amino acids or peptides refers to the naturally occurring, or L-isomer, of the amino acids or peptides. However, the present compounds and methods are not limited thereto and D-isomer amino acid residues can take the place of some or all of L-amino acids. In like manner, mixtures of D- and L-isomers can also be used. In the embodiments wherein the amino acid is proline, R$^7$ together with R$^6$ forms a pyrrolidine ring structure. R$^6$ can be any of the naturally occurring amino acid side chains, for example —CH$_3$ (alanine), —(CH$_2$)$_3$NHCNH$_2$NH (arginine), —CH$_2$CONH$_2$ (asparagine), —CH$_2$COOH (aspartic acid,), —CH$_2$SH (cysteine), —(CH$_2$)$_2$CONH$_2$ (glutamine), —(CH$_2$)$_2$COOH (glutamic acid), —H (glycine), —CHCH$_3$CH$_2$CH$_3$ (isoleucine), —CH$_2$CH(CH$_3$)$_2$ (leucine), —(CH$_2$)$_4$NH$_2$ (lysine), —(CH$_2$)$_2$SCH$_3$ (methionine), —CH$_2$Ph (phenylalanine), —CH$_2$OH (serine), —CHOHCH$_3$ (threonine), —CH(CH$_3$)$_2$ (valine),

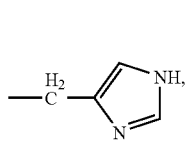

(histidine)

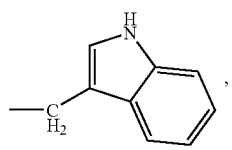

(tryptophan)

, and

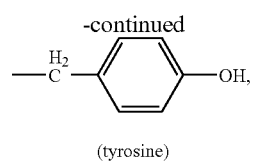

(tyrosine)

—(CH$_2$)$_3$NHCONH$_2$ (citrulline) or —(CH$_2$)$_3$NH$_2$ (ornithine). Ph designates a phenyl group.

In the above compounds, R$^7$ and R$^8$ may be the same or different and are selected from the group consisting of H, and —COCHR$^9$NR$^{10}$R$^{11}$, wherein R$^9$ is a side chain of amino acid, R$^{10}$ and R$^{11}$ may be the same or different and are selected from the group consisting of H, and —COCHR$^{12}$NR$^{13}$R$^{14}$, wherein R$^{12}$ is an amino acid side chain, R$^{13}$ and R$^{14}$ may be the same or different and are independently selected from the group consisting of H, and —COCHR$^{15}$NH$_2$. One skilled in the art will realize that the peptide chains can be extended on the following scheme to the desired length and include the desired amino acid residues.

In the embodiments where either or both of OR$^2$ and OR$^3$ groups form an ester of a peptide, such as dipeptide, tripeptide, tetrapeptide, etc. the peptides can be either homopeptides, i.e., repeats of the same amino acid, such as arginyl-arginine, or heteropeptides, i.e., made up of different combinations of amino acids. Examples of heterodipeptides include alanyl-glutamine, glycyl-glutamine, lysyl-arginine, etc. As will be understood by the skilled artisan when only one R$^7$ and R$^8$ includes a peptide bond to further amino acid, such as in the di, tri and tetrapeptides, the resulting peptide chain will be linear. When both R$^7$ and R$^8$ include a peptide bond, then the peptide can be branched.

In still other embodiments of the present compounds R$^1$ is H and one of R$^2$ or R$^3$ is a phosphate group or H while the other R$^2$ or R$^3$ is a group such the OR$^2$ or OR$^3$ is an ester of an amino acid, such as an ester of glycine or alanine.

Pharmaceutically acceptable salts of these compounds as well as pharmaceutical formulation of these compounds are also provided.

Compounds of formula I and methods of making such compounds are disclosed, for example, in U.S. Pat. Nos. 7,384,978, 7,417,070 and 7,544,713 and PCT publication no. WO 2005/007081.

In some embodiments, the active agent may be (+) treprostinil, which has the following structure:

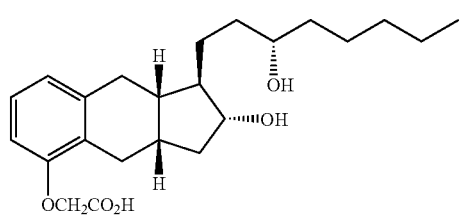

Treprostinil is a chemically stable analog of prostacyclin, and as such is a potent vasodilator and inhibitor of platelet aggregation. The sodium salt of treprostinil, (1R,2R,3aS,9aS)-[[2,3,3a,4,9,9a-Hexahydro-2-hydroxy-1-[(3S)-3-hydroxyoctyl]-1H-benz[f]inden-5-yl]oxy]acetic acid monosodium salt, is sold as a solution for injection as Remodulin® which has been approved by the Food and Drug Administration (FDA) for treatment of pulmonary hypertension.

Treprostinil was first described in U.S. Pat. No. 4,306,075. U.S. Pat. No. 5,153,222 discloses use of treprostinil for treatment of pulmonary hypertension. U.S. Pat. No. 5,234,953 discloses treatment of congestive heart failure with treprostinil. U.S. Pat. Nos. 6,765,117 and 6,809,223 disclose stereoselective process for treprostinil synthesis. U.S. Pat. Nos. 6,521,212 and 6,756,033 describe administration of treprostinil by inhalation for treatment of pulmonary hypertension, peripheral vascular disease and other diseases and conditions. U.S. Pat. No. 6,054,486 discloses treatment of peripheral vascular disease with treprostinil. U.S. Pat. No. 6,803,386 discloses administration of treprostinil for treating cancer such as lung, liver, brain, pancreatic, kidney, prostate, breast, colon and head-neck cancer. U.S. patent application publication no. 2005/0165111 discloses treprostinil treatment of ischemic lesions. U.S. Pat. No. 7,199,157 discloses that treprostinil treatment improves kidney functions. U.S. patent application publication no. 2005/0282903 discloses treprostinil treatment of diabetic neuropathic foot ulcers. U.S. patent application publication no. 2008/0280986 discloses treatment of interstitial lung disease with reprostinil. U.S. patent application publication no. 2008/0200449 discloses administration of Treprostinil via a metered dose inhaler. US patent application publication no. 2009/0163738 discloses an alternative process for preparation treprostinil.

In some embodiments, the active agent can be (−)-treprostinil, the enantiomer of (+)-treprostinil.

In some embodiments, the active agent may be a pharmaceutically acceptable salt of Treprostinil.

In a preferred embodiment, the active agent can be the diethanolamine salt of treprostinil. The diethanolamine salt of treprostinil can be in an amorphous or a crystalline state. In the crystalline state, the diethanolamine salt of treprostinil can have two polymorphs, with two forms, A and B, which are disclosed in U.S. Pat. Nos. 7,384,978, 7,417,070 and 7,544,713. Of the two forms, B is preferred. Thus, a particularly preferred embodiment of the present invention may be form B of treprostinil diethanolamine.

Prostacyclin analogs, such as compounds of formula I, may be used in promoting vasodilation, inhibiting platelet aggregation and thrombus formation, stimulating thrombolysis, inhibiting cell proliferation (including vascular remodeling), providing cytoprotection, preventing atherogenesis and inducing angiogenesis. Through these prostacyclin-mimetic mechanisms, the compounds of formula I may be used in the treatment of/for: pulmonary hypertension, ischemic diseases (e.g., peripheral vascular disease, Raynaud's phenomenon, Scleroderma, myocardial ischemia, ischemic stroke, renal insufficiency), heart failure (including congestive heart failure), conditions requiring anticoagulation (e.g., post MI, post cardiac surgery), thrombotic microangiopathy, extracorporeal circulation, central retinal vein occlusion, atherosclerosis, inflammatory diseases (e.g., COPD, psoriasis), hypertension (e.g., preeclampsia), reproduction and parturition, cancer or other conditions of unregulated cell growth, cell/tissue preservation and other emerging therapeutic areas where prostacyclin treatment appears to have a beneficial role. These compounds may also demonstrate additive or synergistic benefit in combination with other cardiovascular agents (e.g., calcium channel blockers, phosphodiesterase inhibitors, endothelial antagonists, antiplatelet agents).

The present invention can be illustrated in more detail by the following example, however, it should be understood that the present invention is not limited thereto.

Example

Stability tests were performed on 1-mg tablets of treprostinil diethanoloamine. The tablet were placed either in 45 cc white HDPE bottles with desiccant or blistered using ACLAR® UltRx 3000 (3.00 mil chlorotrifluoroethylene (CTFE) homopolymer) film. The tablets were stored in either bottles with desiccant or blistered packages in an environment with a temperature of 40° C. and 75% relative humidity (40 C/75% RH). A level of impurities was measured in 3 and 6 months in both tablets stored in the bottles with desiccant and tablets stored in the blistered packages. The results are presented in Table 1.

TABLE 1

| Impurity | Initial | 3 months at 40 C./75% RH | | 6 months at 40 C./75% RH Aclar | |
|---|---|---|---|---|---|
| | | Bottle with desiccant | Aclar ® Ultrx 3000 | Bottle with desiccant | Aclar ® Ultrx 3000 |
| RRT 0.29 | | 0.12 | 0.10 | 0.17 | 0.11 |
| RRT 0.37 | | 0.12 | 0.10 | 0.11 | |
| RRT 0.48 | | | | 0.13 | |
| RRT 0.55 | | 0.10 | 0.14 | 0.19 | 0.20 |
| UT-15 BHEA | | 0.38 | 0.20 | 0.51 | |
| RRT 0.70 | | 0.23 | 0.22 | 0.35 | 0.30 |
| RRT 0.72 | | 0.22 | 0.20 | 0.42 | 0.38 |
| 3AU90 | | | | 0.12 | 0.17 |
| UT-15 CPK | | 0.22 | 0.13 | 0.26 | 0.22 |
| UT-15 SCK | | | | 0.12 | |
| 750W93 | | 0.10 | | 0.18 | 0.14 |
| 751W93 | | | | 0.12 | 0.10 |
| Total | 0.00 | 1.40 | 1.10 | 2.70 | 1.60 |
| Moisture (%) | 2.80 | 3.10 | 4.10 | 3.10 | 4.30 |

The identified impurities in Table 1 are as follows: RRT 0.29—benzyl hydroxy treprostinil, RRT 0.37—currently unknown, RRT 0.48—xylitol ester of treprostinil, RRT 0.55—xylitol ester of treprostinil, UT-15 BHEA—is the amide of treprostinil with the counterion, RRT 0.70—xylitol ester of treprostinil, RRT 0.72—xylitol ester of treprostinil, 3AU90 is an isomer of treprostinil, UT-15 CPK is the cyclopentyl ketone of treprostinil, UT-15 SCK is the side chain ketone of treprostinil, 750W93 is an ester dimer of treprostinil, and 751W93 is a 3-hydroxy dimer of treprostinil. Although the blister film was more permeable to moisture than the bottles, it was surprisingly found that the tablets, that were stored in the blistered packages, had lower level of impurities, compared to the tablets, that were stored in the bottles. These results are surprising because they go against a conventional approach, that formulation scientists utilize, minimizing moisture exposure to minimize a degradation of an active ingredient in solid formulations.

Additional stability tests were performed on 1-mg tablets of treprostinil diethanoloamine that were placed either in 45 cc white HDPE bottles with or without desiccant or blistered using ACLAR® UltRx 3000 (3.00 mil chlorotrifluoroethylene (CTFE) homopolymer) film. The tablets were stored in either bottles with or without desiccant or blistered packages in an environment with a temperature of 40° C. and 75% relative humidity (40 C/75% RH). The bottles with desiccant have the least amount of moisture exposure to the tablets, followed by bottles without desiccant, and the highest moisture environment for the tablets is the blisters. The moisture levels of the tablets at one and three months were measured for each packaging condition. As the moisture level increases, especially above 3%, that the impurity levels decrease for each as well as the total, see Table 2. This result is surprising and counterintuitive because typically for solid-dosage forms minimization of moisture levels is recommended.

TABLE 2

| Time | | Tablets in bottles with desiccant | | Tablets in bottles without desiccant | | Tablets in blisters | |
|---|---|---|---|---|---|---|---|
| | | Initial | 3 month | Initial | 3 month | Initial | 3 month |
| Assay by HPLC | Release: Not less than 95.0% and not more than 105.0% of labeled strength. Stability: Not less than 90.0% and not more than 110% of labeled strength | 100.3 | 95.8 | 99.7 | 97.8 | 99.8 | 98.4 |
| Impurities and Related Substances | Impurity I (RRT 0.30) | ND | 0.14 | ND | 0.12 | ND | 0.12 |
| | Impurity II (RRT 0.38) | ND | 0.15 | ND | 0.13 | ND | 0.12 |
| | Impurity IV (RRT 0.56) | ND | 0.12 | ND | 0.13 | ND | 0.15 |
| | UT-15 Amide | ND | 0.30 | ND | 0.22 | ND | ND |
| | Impurity V (RRT 0.70) | ND | 0.15 | ND | ND | ND | ND |
| | Impurity VI (RRT 0.72) | ND | 0.21 | ND | 0.15 | ND | 0.14 |
| | 3AU90 | ND | 0.12 | ND | ND | ND | ND |
| | UT-15 CPK | ND | 0.11 | ND | 0.10 | ND | ND |
| | Total Impurities: NMT 3.0% | ND | 1.30 | ND | 0.85 | ND | 0.53 |
| Water Content by Karl Fischer | | 3.2 | 2.2 | 2.9 | 2.7 | 3.1 | 3.5 |

Table 3 provides the stability data for 1-mg lots that were placed on stability with a 1-gram desiccant at 40 C/75% RH. Table 3 also provides the moisture levels. Table 4 provides the stability data for 1-mg lots that were placed on stability without a desiccant at 40 C/75% RH. Also provided are the moisture levels at each time point. One can see the moisture level slowly rises over time without desiccant and to a much lesser extent with desiccant. The impurity profile looks better without desiccant.

TABLE 3

| Test | Method | Specification | Clinical Lot | Stability Lot | Initial | 1 months | 3 months | 6 months |
|---|---|---|---|---|---|---|---|---|
| Appearance | ATM-MAG-M0003 | A biconvex, round, film-coated, white tablet with a hole only on one side and may have imprinting on one side | 0702276 | 0702406 | Conforms | Conforms | Conforms | Conforms |
| | | | 0702277 | 0702407 | Conforms | Conforms | Conforms | Conforms |
| | | | 0703093 | 0703802 | Conforms | Conforms | Conforms | Conforms |
| Assay by HPLC | ATM-LRR-M0041 | Release: Not less than 95.0% and not more than 105.0% of labeled strength. Stability: Not less than 90.0% and not more than 110% of labeled strength | 0702276 | 0702406 | 100.3 | 98.7 | 95.8 | 96.3 |
| | | | 0702277 | 0702407 | 100.3 | 100.9 | 98.5 | 97.4 |
| | | | 0703093 | 0703802 | 101.0 | 99.2 | 99.2 | 97.6 |
| Related Substance by HPLC | ATM-LRR-M0042 | Impurity Ia (RRT 0.2) | 0702276 | 0702406 | ND | ND | ND | ND |
| | | Impurity I (RRT 0.30) | | | ND | ND | 0.14 | 0.21 |
| | | Impurity II (RRT 0.38) | | | ND | 0.12 | 0.15 | 0.17 |
| | | Impurity III (RRT 0.49) | | | ND | ND | ND | 0.10 |
| | | Impurity IV (RRT 0.56) | | | ND | ND | 0.12 | 0.22 |
| | | UT-15 BHEA | | | ND | 0.16 | 0.30 | 0.52 |
| | | Impurity V (RRT 0.70) | | | ND | ND | 0.15 | 0.28 |
| | | Impurity VI (RRT 0.72) | | | ND | ND | 0.21 | 0.31 |
| | | Impurity VII (RRT 0.87) | | | ND | ND | ND | ND |
| | | 97W86 | | | ND | ND | ND | ND |
| | | 3AU90 | | | ND | ND | 0.12 | ND |
| | | UT-15 CPK | | | ND | ND | 0.11 | 0.25 |
| | | Impurity VIII (RRT 1.11) | | | ND | ND | ND | ND |
| | | UT-15 SCK | | | ND | ND | ND | 0.12 |
| | | Impurity IX (RRT 1.30) | | | ND | ND | ND | ND |
| | | 98W86 | | | ND | ND | ND | ND |
| | | 750W93 | | | ND | ND | ND | 0.11 |
| | | Total Impurities: NMT 3.0% | | | ND | 0.28 | 1.30 | 2.30 |
| | | Impurity Ia (RRT 0.2) | 0702277 | 0702407 | ND | ND | ND | ND |
| | | Impurity I (RRT 0.30) | | | ND | ND | 0.14 | 0.21 |
| | | Impurity II (RRT 0.38) | | | ND | 0.12 | 0.15 | 0.17 |
| | | Impurity III (RRT 0.49) | | | ND | ND | ND | 0.10 |
| | | Impurity IV (RRT 0.56) | | | ND | ND | 0.11 | 0.22 |
| | | UT-15 BHEA | | | ND | 0.16 | 0.31 | 0.51 |
| | | Impurity V (RRT 0.70) | | | ND | ND | 0.14 | 0.29 |
| | | Impurity VI (RRT 0.72) | | | ND | ND | 0.22 | 0.31 |
| | | Impurity VII (RRT 0.87) | | | ND | ND | ND | ND |

TABLE 3-continued

| Test | Method | Specification | Clinical Lot | Stability Lot | Initial | 1 months | 3 months | 6 months |
|---|---|---|---|---|---|---|---|---|
| | | 97W86 | | | ND | ND | ND | ND |
| | | 3AU90 | | | ND | ND | 0.12 | ND |
| | | UT-15 CPK | | | ND | ND | 0.12 | 0.25 |
| | | Impurity VIII (RRT 1.11) | | | ND | ND | ND | ND |
| | | UT-15 SCK | | | ND | ND | ND | 0.13 |
| | | Impurity IX (RRT 1.30) | | | ND | ND | ND | ND |
| | | 98W86 | | | ND | ND | ND | ND |
| | | 750W93 | | | ND | ND | ND | 0.10 |
| | | Total Impurities: NMT 3.0% | | | ND | 0.28 | 1.30 | 2.30 |
| Water Content by Karl Fischer | ATM-LRR-M0037 | Not more than 5.0% | 0702276 0702277 0703093 | 0702406 0702407 0703802 | 3.2 3.1 3.5 | 3.1 2.8 2.5 | 2.2 3.0 2.5 | 2.8 2.7 2.8 |

TABLE 4

| Test | Method | Specification | Clinical Lot | Stability Lot | Initial | 3 months | 6 months |
|---|---|---|---|---|---|---|---|
| Appearance | PPD# M4281 | A biconvex, round, film-coated, white tablet with a hole only on one side and may have imprinting on one side | 0802503 0805096 | 0803176 0805724 | Conforms Conforms | Conforms Conforms | Conforms Conforms |
| Assay by HPLC | PPD# M4239 | Release: Not less than 95.0% and not more than 105.0% of labeled strength. Stability: Not less than 90.0% and not more than 110% of labeled strength | 0802503 0805096 | 0803176 0805724 | 99.7 102.2 | 97.8 100.7 | 97.5 100.3 |
| Related Substance by HPLC | PPD# M4239 | Impurity Ia (RRT 0.2) | 0802503 | 0803176 | ND | ND | ND |
| | | Impurity I (RRT 0.30) | | | ND | 0.12 | 0.18 |
| | | Impurity II (RRT 0.38) | | | ND | 0.13 | 0.10 |
| | | Impurity III (RRT 0.49) | | | ND | ND | ND |
| | | Impurity IV (RRT 0.56) | | | ND | 0.13 | 0.17 |
| | | UT-15 BHEA | | | ND | 0.22 | 0.12 |
| | | Impurity V (RRT 0.70) | | | ND | ND | 0.21 |
| | | Impurity VI (RRT 0.72) | | | ND | 0.15 | 0.28 |
| | | Impurity VII (RRT 0.87) | | | ND | ND | ND |
| | | 97W86 | | | ND | ND | ND |
| | | 3AU90 | | | ND | ND | ND |
| | | UT-15 CPK | | | ND | 0.10 | 0.27 |
| | | Impurity VIII (RRT 1.11) | | | ND | ND | ND |
| | | UT-15 SCK | | | ND | ND | ND |
| | | Impurity IX (RRT 1.30) | | | ND | ND | ND |
| | | 98W86 | | | ND | ND | ND |
| | | 750W93 | | | ND | ND | ND |
| | | Total Impurities: NMT 3.0% | | | ND | 0.85 | 1.30 |
| | | Impurity Ia (RRT 0.2) | 0805096 | 0805724 | ND | ND | ND |
| | | Impurity I (RRT 0.30) | | | ND | 0.13 | 0.17 |
| | | Impurity II (RRT 0.38) | | | ND | 0.15 | ND |
| | | Impurity III (RRT 0.49) | | | ND | ND | ND |
| | | Impurity IV (RRT 0.56) | | | ND | 0.14 | 0.23 |
| | | UT-15 BHEA | | | ND | 0.14 | 0.18 |
| | | Impurity V (RRT 0.70) | | | ND | ND | 0.21 |
| | | Impurity VI (RRT 0.72) | | | ND | 0.16 | 0.31 |
| | | Impurity VII (RRT 0.87) | | | ND | ND | ND |
| | | 97W86 | | | ND | ND | ND |
| | | 3AU90 | | | ND | ND | ND |
| | | UT-15 CPK | | | ND | ND | 0.25 |
| | | Impurity VIII (RRT 1.11) | | | ND | ND | ND |
| | | UT-15 SCK | | | ND | ND | 0.11 |
| | | Impurity IX (RRT 1.30) | | | ND | ND | ND |
| | | 98W86 | | | ND | ND | ND |
| | | 750W93 | | | ND | ND | ND |
| | | Total Impurities: NMT 3.0% | | | ND | 0.72 | 1.4 |
| Water Content by Karl Fischer | PPD# M4247 | Not more than 5.0% | 0802503 | 0803176 | 2.9 | 2.7 | 2.9 |
| | | | 0805096 | 0805724 | 2.5 | 2.8 | 3.4 |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All the publications, patent applications and patents cited in this specification are incorporated herein by reference in their entirety.

What is claimed is:

1. A pharmaceutical product comprising
a pharmaceutical packaging; and
a solid formulation inside the packaging, wherein the formulation comprises an active agent that is treprostinil diethanolamine, wherein the packaging is configured to maintain a moisture level in the solid formulation of greater than 3% and no more than 7%.

2. The pharmaceutical product of claim 1, wherein said formulation further comprises at least one pharmaceutically acceptable excipient.

3. The pharmaceutical product of claim 2, wherein said at least one excipient comprises at least one of maltodextrin and xylitol.

4. The pharmaceutical product of claim 1, wherein the packaging in configured to maintain the moisture level of no less than 3.5% and no more than 6%.

5. The pharmaceutical product of claim 1, wherein the packaging in configured to maintain the moisture level of no less than 3.5% and no more than 4.5%.

6. The pharmaceutical product of claim 1, wherein said packaging is a bottle packaging.

7. The pharmaceutical product of claim 1, wherein said packaging is a blister packaging.

8. The pharmaceutical product of claim 1, wherein the packaging does not include a desiccant.

9. A pharmaceutical product comprising:
(a) a pharmaceutical packaging;
(b) a solid formulation inside the packaging, wherein the formulation comprises a active agent that is treprostinil diethanolamine; and
(c) a desiccant inside the packaging, wherein an amount of the desiccant in the packaging is less than an effective amount for maintaining a relative humidity level inside the packaging for a storage time of the formulation below 40%.

10. The pharmaceutical product of claim 9, wherein said formulation further comprises at least one pharmaceutically acceptable excipient.

11. The pharmaceutical product of claim 10, wherein said at least one excipient comprises at least one of maltodextrin and xylitol.

12. The pharmaceutical product of claim 9, wherein the packaging is a bottle.

13. The pharmaceutical product of claim 9, wherein the amount of the desiccant in the packaging is less than an effective amount for maintaining a humidity level in the packaging for 24 months below 40%.

14. The pharmaceutical product of claim 13, wherein the amount of the desiccant in the packaging is at least two times less than an effective amount for maintaining a humidity level in the packaging for 24 months below 40%.

15. A storage method comprising:
storing a solid formulation inside a pharmaceutical packaging, wherein the formulation comprises an active agent that is treprostinil diethanolamine; wherein a moisture level in the solid formulation after said storing is greater than 3% and no more than 7%.

16. The storage method of claim 15, wherein said formulation further comprises at least one pharmaceutically acceptable excipient.

17. The storage method of claim 16, wherein said at least one excipient comprises at least one of maltodextrin and xylitol.

18. The storage method of claim 15, wherein the moisture level in the solid formulation after said storing is no less than 3.5% and no more than 6%.

19. The storage method of claim 15, wherein the moisture level in the solid formulation after said storing is of no less than 3.5% and no more than 4.5%.

20. The storage method of claim 15, wherein said storing lasts at least 12 months.

21. The storage method of claim 15, wherein said storing lasts at least 24 months.

22. The storage method of claim 15, wherein the solid formulation is stored inside the packaging together with a desiccant, wherein an amount of the desiccant is less that an effective amount for maintaining a humidity level inside the packaging during said storing below 40%.

23. The storage method of claim 15, wherein said packaging is a bottle packaging.

24. The storage method of claim 15, wherein said packaging is a blister packaging.

25. A storage method comprising:
storing a solid formulation and a desiccant inside a pharmaceutical packaging, wherein the formulation comprises an active agent that is treprostinil diethanolamine; wherein an amount of the desiccant is less that an effective amount for maintaining a relative humidity level inside the packaging during said storing below 40%.

26. The storage method of claim 25, wherein said formulation further comprises at least one pharmaceutically acceptable excipient.

27. The storage method of claim 26, wherein said at least one excipient comprises at least one of maltodextrin and xylitol.

28. The storage method of claim 25, wherein a moisture level in the solid formulation after said storing is no less than 3.5% and no more than 6%.

29. The storage method of claim 25, wherein a moisture level in the solid formulation after said storing is of no less than 3.5% and no more than 4.5%.

30. The storage method of claim 25, wherein said storing lasts at least 12 months.

31. The storage method of claim 25, wherein said storing lasts at least 24 months.

32. The storage method of claim 25, wherein said packaging is a bottle packaging.

33. The storage method of claim 25, wherein said packaging is a blister packaging.

* * * * *